(12) United States Patent
Guillot

(10) Patent No.: US 7,540,850 B2
(45) Date of Patent: Jun. 2, 2009

(54) ORTHOSIS FOR SCAR TISSUE TREATMENT

(76) Inventor: Michel Guillot, 119 Avenue de Lyon, F-01960, Peronnas (FR)

( * ) Notice: Subject to any disclaimer, the term of this patent is extended or adjusted under 35 U.S.C. 154(b) by 584 days.

(21) Appl. No.: 10/488,832

(22) PCT Filed: Sep. 5, 2002

(86) PCT No.: PCT/FR02/03010

§ 371 (c)(1), (2), (4) Date: Sep. 7, 2004

(87) PCT Pub. No.: WO03/022184

PCT Pub. Date: Mar. 20, 2003

(65) Prior Publication Data

US 2005/0010149 A1 Jan. 13, 2005

(30) Foreign Application Priority Data

Sep. 7, 2001 (FR) .................... 01 11574

(51) Int. Cl.
*A61F 5/00* (2006.01)
(52) U.S. Cl. ...................................... 602/60
(58) Field of Classification Search ............. 602/60, 602/41–44, 53, 57, 58, 19; 424/402, 78.02, 424/78.06, 443, 445, 446–449; 606/151, 606/213–215, 110, 113, 201, 202, 204.15; 601/132–134, 118–123; 128/888, 889; D24/200, D24/211, 214
See application file for complete search history.

(56) References Cited

U.S. PATENT DOCUMENTS

| 2,344,021 | A | * | 3/1944 | Bouziane | 606/201 |
| 3,026,874 | A | * | 3/1962 | Stevens | 604/305 |
| 4,120,297 | A | * | 10/1978 | Rabischong et al. | 602/19 |
| 4,436,089 | A | * | 3/1984 | Schmid | 602/53 |
| 4,592,345 | A | * | 6/1986 | Wahl | 601/57 |
| 5,466,250 | A | * | 11/1995 | Johnson et al. | 607/104 |
| 5,503,908 | A | * | 4/1996 | Faass | 428/198 |

(Continued)

FOREIGN PATENT DOCUMENTS

CN 1049279 2/1991

(Continued)

OTHER PUBLICATIONS

International Search Report for corresponding PCT application WO 03/022184—Mar. 2003—6 pages.

(Continued)

*Primary Examiner*—Steven O Douglas
(74) *Attorney, Agent, or Firm*—Polster, Lieder, Woodruff & Lucchesi, L.C.

(57) ABSTRACT

The invention concerns an orthosis (1) for preventing and treating hypertrophy (22), keloid, bridle, scar retraction, to improve functional and aesthetic quality and enable scar growth. Said orthosis (2) enables to enhance [sic] the quality of healing, to decrease the number of repair surgical procedures for functional purposes. It provides the patient with more aesthetic movements. Said orthosis is characterized in that it comprises one or more treatment units (2) having a mechanical pressing action (13) on the scar and an activator (3) for enhancing the action of the units (2), for increasing their attachment, for transmitting traction derived from the patient's movements.

21 Claims, 6 Drawing Sheets

U.S. PATENT DOCUMENTS

Figure 1:
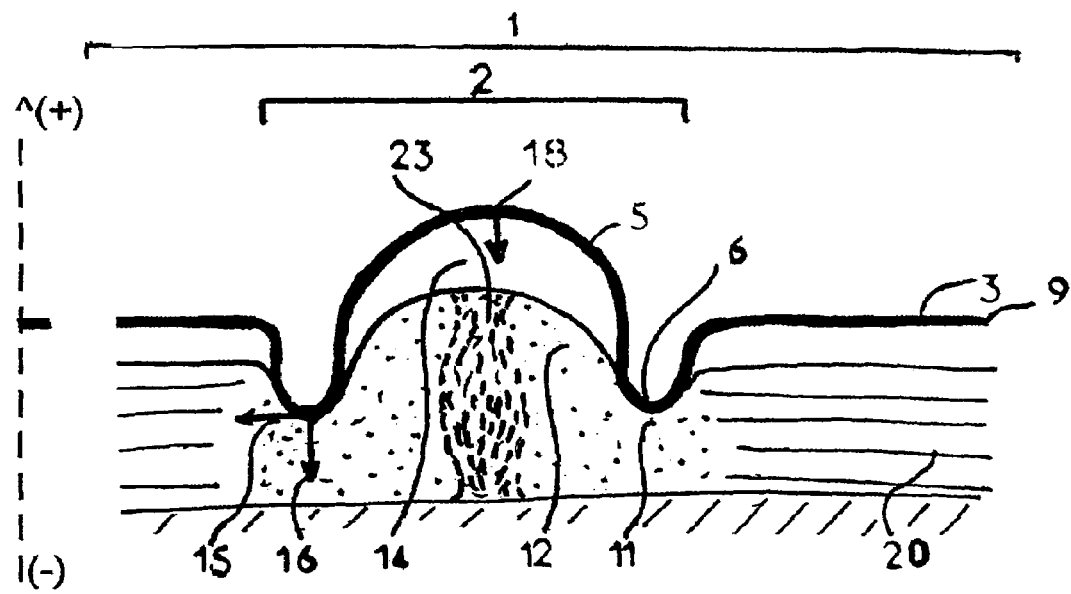

| | | | |
|---|---|---|---|
| 5,746,707 A | 5/1998 | Eck | |
| 5,873,890 A * | 2/1999 | Porat | 606/201 |
| 6,013,094 A | 1/2000 | DeCubber et al. | |
| 6,238,413 B1 * | 5/2001 | Wexler | 606/204.15 |
| 6,274,786 B1 * | 8/2001 | Heller | 602/41 |
| 6,274,787 B1 * | 8/2001 | Downing | 602/41 |
| 6,461,221 B1 * | 10/2002 | Stilwell et al. | 450/57 |

FOREIGN PATENT DOCUMENTS

| | | |
|---|---|---|
| EP | 0409587 | 9/1993 |
| FR | 2670668 | 6/1992 |

OTHER PUBLICATIONS

Office Action dated Jul. 1, 2005 in Corresponding Chinese App. No. 028216342 and an English Translation Thereof.

* cited by examiner

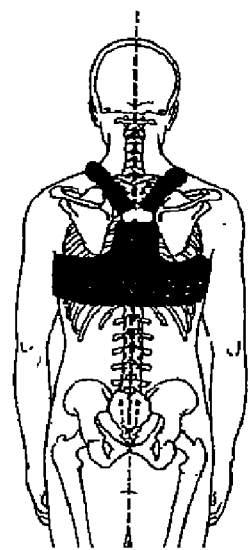
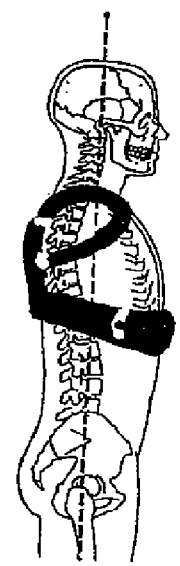
FIG7    FIG8
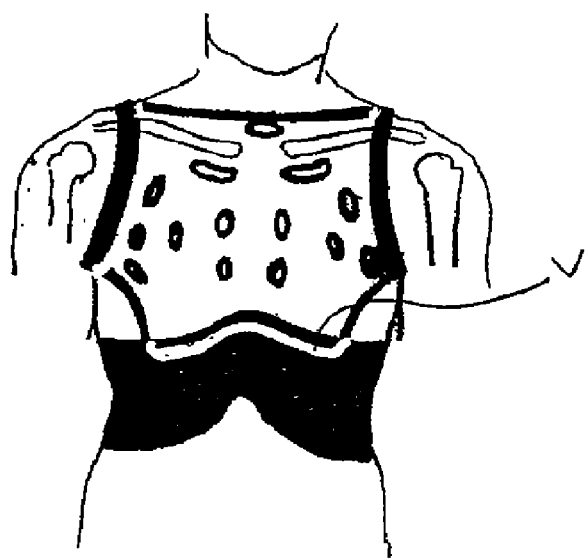
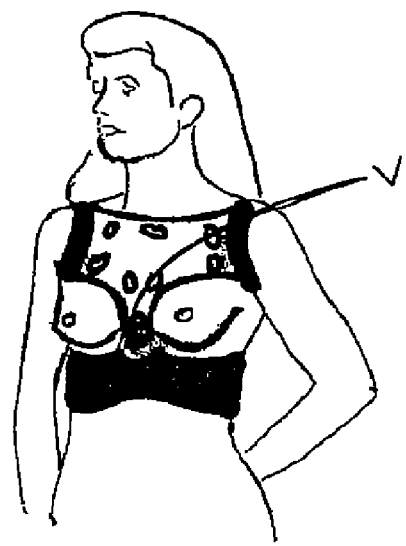
FIG 9    FIG10

ORTHOSIS FOR SCAR TISSUE TREATMENT

The present invention is designed to treat, in a preventive or curative way, hypertrophy, retraction, fibrosis, etc. that are secondary to deep lesions of the skin and soft tissues.

We see in patent EP824 016 that pressure exerted by pressure bands has been shown to be insufficient, whereas rigid strips manufactured of hard plastic material, according to proper accepted practice, prevent healing of the skin. To overcome these drawbacks, the present invention provides a device that treats scar tissues, and comprises a covering device, made of a soft compatible polymer, which comes into contact with the scar tissue, and a support element made of rigid material. An inflatable device, placed between the soft covering device, and the rigid support element, presses the soft-material covering device onto the scar tissues with optimal pressure, which makes wearing the device comfortable over a long period of scarring process. The device is applied in particular to a patient's face, so as to distribute pressure between bony projecting areas and recessed areas, in order to make wearing this device more bearable for the patient. Moreover, this mask can be heavy and complex; both in its construction and its adjustment as well as its upkeep. Such a device is difficult to disinfect and is the source of numerous infections.

In order to overcome these drawbacks and encourage proper and rapid dermal scarring, the invention offers a selective means of pressure therapy, and is innovative because it is distinguished by these facts known today by the specificity of its actions. It can be easily recognized by the appearance of its compressive surface. This surface consists of grooves that are inconsistent in their depth and width; they are indicated by lines that vary in curve, size, and arrangement which delineate enclosed spaces that are not necessarily joined or closed. These sinuosities in the compression area face the scarred area being treated, or are on the edge of the healthy skin area. This orthosis exerts selective prolonged pressure and allows its components to be controlled.

It is especially useful for the treatment of scars from deep burns, starting on the fifteenth day of neo-epidermization or transplant during the neodermal scarring phase. It allows dermal scarring to be controlled. Among other things, scarring complications are aggravated by movements and growth. This treatment improves a good number of scars or subcutaneous lesions of varying etiologies such as: surgical incisions, dermabrasions, tumor excisions or cutaneous malformations, post-laser-therapy scarring, stretch marks, wrinkles, tendinitis, Dupuytren's contraction, or any other condition which might result in a significant alteration of the base membrane, the dermis and the soft tissues. It acts on scars in many different ways, which are modulatable by area. It specifically treats each scarring abnormality, notably anchorages or areas of adherence for slip planes, adhesions, and fibroses and re-coordinates them. Each scarring complication, localization, and shape has a corresponding groove arrangement. The wealth of these grooves translates the complexity of its action, in contrast to standard means of therapy. It creates local limited pressures, well-tolerated doses that are reproducible and capable of targeting selected lesions between scars. It administers pressure such that, when cicatricial blanching exists opposite the groove bases, which translates into an effective neovascular compression, which causes ischemia but not necrosis. It causes hyperpressure points on the scar. Average pressure at groove contact is greater than that created with standard pressure therapy techniques: pressure garments, transparent rigid compresses, including those that are pneumo-hydraulic due to their overall homogeneous action, which is related to their significant and smooth support surface. Its action allows discriminating compression depending on the location, and a modulated neocapillary pressure regulation by area, which refines the possibilities for controlled ischemia. Moreover, it takes into consideration the functional stresses that are specific to the treated area. Overall, it coordinates the tensions between scars and optimizes the scars' mechanical properties. The orthosis offers the advantage of being extra-corporeal, non-invasive for the patient, without other means of action except for the pressure being exerted. It acts favorably on points of flexion.

Often life threatening in the past, burns in a child can today still lead to functional and aesthetic difficulties, with many months of restrictive treatment involved as well. Interest in orthosis goes beyond the acute inflammation phase. The after-effects remain significant and growth is the dominant aggravating factor during this time, which corresponds to an absence or near-absence of therapeutic techniques. Negligence leads to cicatricial fibrosis and limitation of slip planes, functional limitations and aesthetic damage that can be significant.

Through its prolonged mechanical action, the invention offers the use of the patient's natural potential to assist in healing. It reduces the initial phase and improves functional and esthetic results. It optimizes scar growth. This invention makes surfaces with significant areas of injury more accessible to treatment, and their progress during growth in young patients.

Initial surgical results, like reparative surgery, depends to a large extent on the neoderma, and in particular the existence of anchorages. Orthosis according to the invention allows the patient to optimize his cicatricial status, to meet functional needs and to access reparative surgery for esthetic purposes.

FIG. 1 shows a scar and a cross-section view of the scarring orthosis (1) centered on a therapeutic unit (2). It shows that all direct pressure (18) on the cupola (5) increases divergent centrifugal pressure (15) and vertical penetration (16) into groove (6). This causes it to act beyond the scar contact surface.

Figure 2:
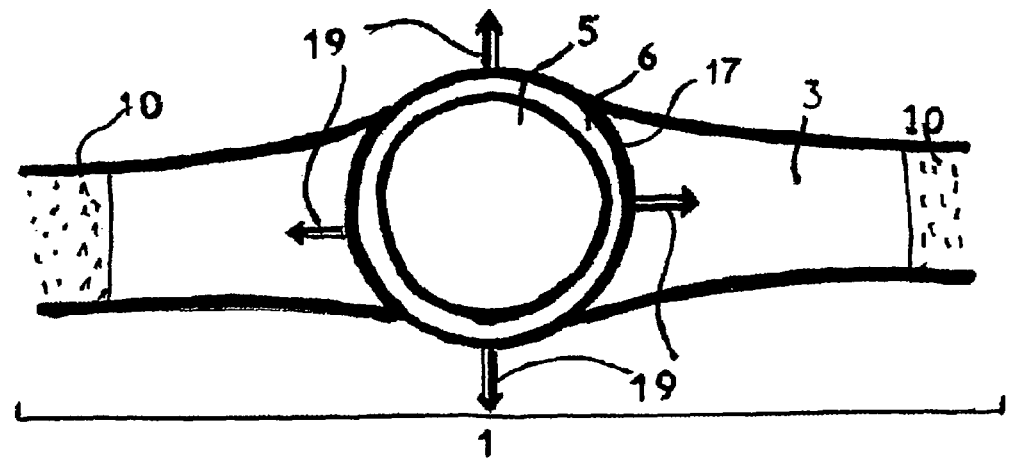

FIG. 2 shows a view from above of the orthosis, centered on unit (2). Activator (3) generally encloses a member segment and is fastened down by means of an adhesive (10). We can see that all traction on the groove edges (17) causes divergent centrifugal inter-cicatricial tensions (19) around the edge of the unit.

Figure 3:
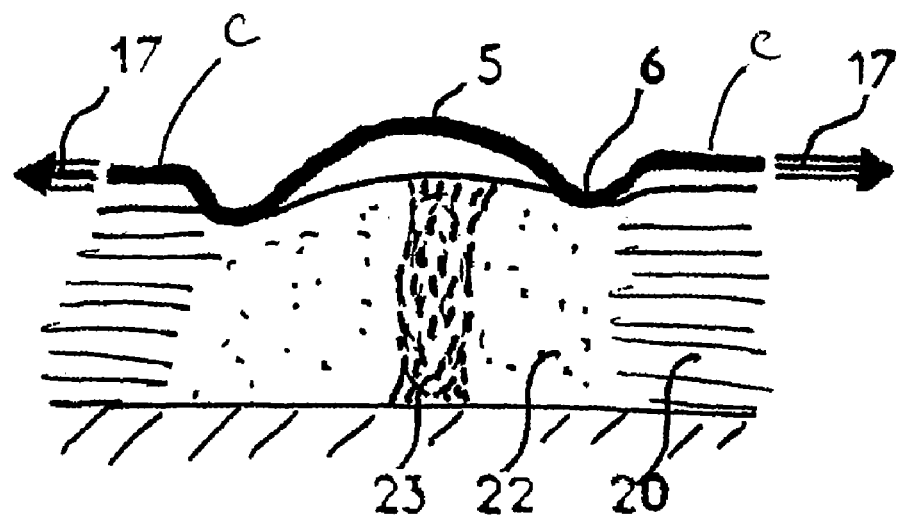

FIG. 3 is a cross-sectional view of the orthosis and the scar, showing activator (3) and its traction action (17) on unit (2). Divergent pressure forces are increased (15) and penetration forces (16) are maintained or increased. The model shows that there are pressures corresponding to the inter-cicatricial tensions (19).

Figure 4:
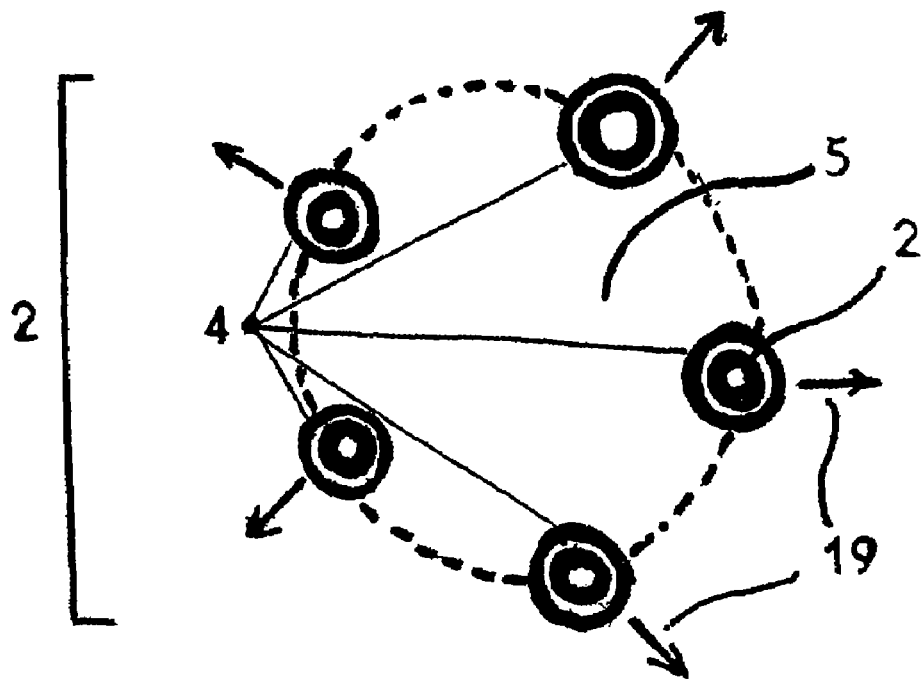

FIG. 4 shows an orthosis composed of an open system where multiple sub-units act together (4) to reproduce the base unit action (2) of the closed system according to the principles of the invention. This is useful for the treatment of large scars.

Figure 5:
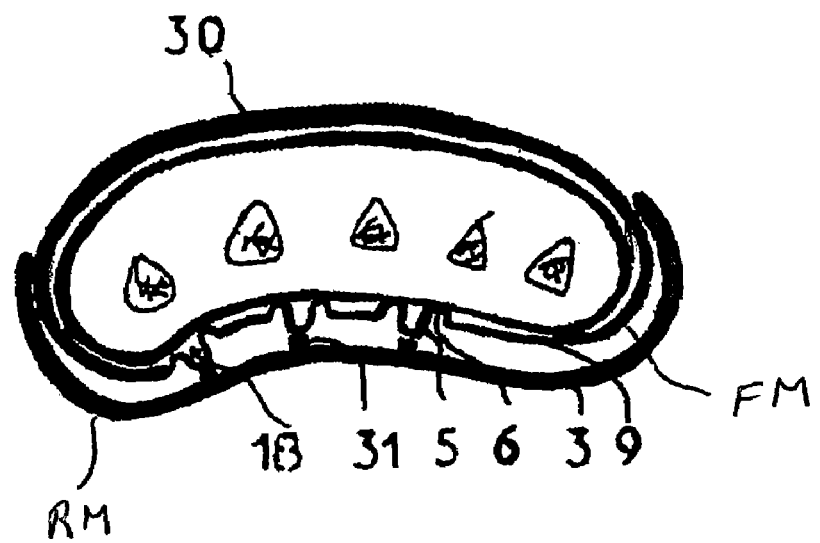

FIG. 5 shows a metacarpal cross-section cut. This hand is equipped with a postural splint (30) that serves as a counter-support and immobilizer in the case of an extended burn of the palm. Plate (9) in this example is modeled in units. It is fastened to the splint edges (30). Activator (3) exerts a pressure (18) on cupolas (5); here through the small nipples (31) whose hardness and size allow the action to be modulated. This orthosis-splint association allows concave areas to be treated.

Figure 6:
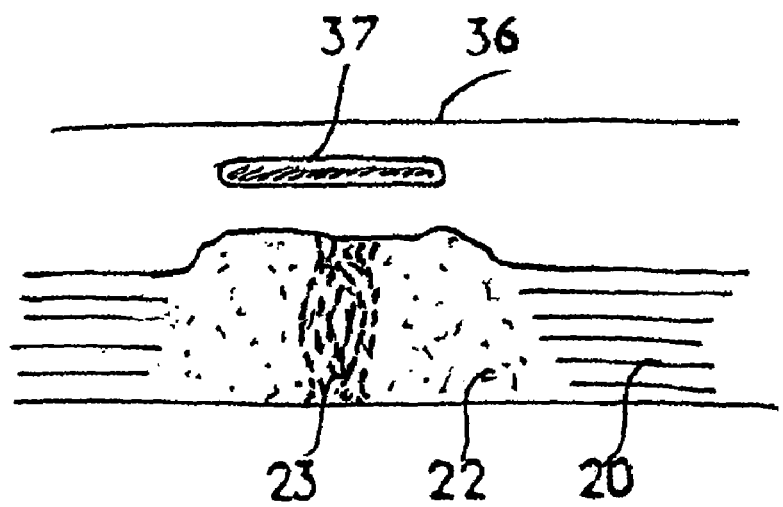

FIG. 6 illustrates the current pressure therapy treatment model that is common to: compressive garments (36), sponges (37), silicones, rigid pneumatic compressions. Compression indication relies on overall testing criteria, which essentially take the scar contours into consideration as well as the scar structure or localization. The overall hypertrophic scar is compressed without modulatable inter-cicatricial pressure differential, divergent action or consideration of area; anchorage (23), hypertrophy (22) . . . .

FIG. 7 shows a back view of a child fitted with an original kyphosis correction device with its thermoformable plastic interscapular hemivalve, molded in the corrected position, and its stuffed underarm cuffs pulling the shoulders.

FIG. 8 shows the profile and the front hemivalve under the ribcage vents. The two valves are jointed so that they move along with breathing motions. Expansion in the vertical axis of the thoracic cage is facilitated at the expense of the antero-posterior. The kyphosis condition is corrected with each inhalation.

FIG. 9 shows the orthosis (1). We note the corrective stuffed armpit cuffs and the anterior valve that covers the last two rib arches and molds a hollow in the top of the abdomen and specifically in the rib louvers. The patient is thus immobilized in the correct corrective position for his kyphoscoliosos, and the orthosis (1) acts effectively on the thoracic scar.

FIG. 10 shows the peri-mammary cutout and the necessary adaptations in adolescents, with attachment of the orthosis onto the corrective elements.

Treatment of breast scarification requires adaptive brassieres and addition of specially shaped units (2).

Figure 11:
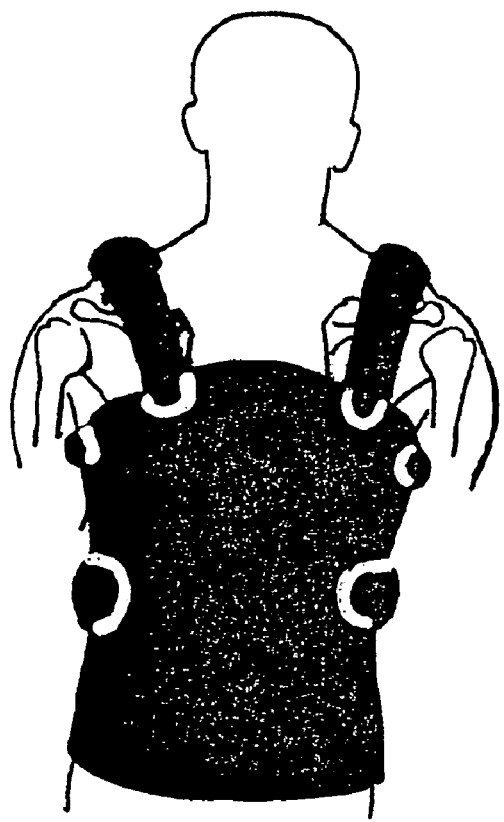

FIG. 11 shows the original different cutout of the posterior valve necessary for an adolescent relating to correction for confirmed kyphoscoliosis. The posterior valve creates supports opposite it: in the middle and at the top of the kyphosis, laterally to the sub-acromial regions and those below the pelvic hemi-basin.

Figure 12:

FIG. 12 is the profile view. The posterior and anterior iliac spines are covered. Orthosis (1) is positioned in a manner similar to that in FIGS. (9) and (10).

Figure 13:
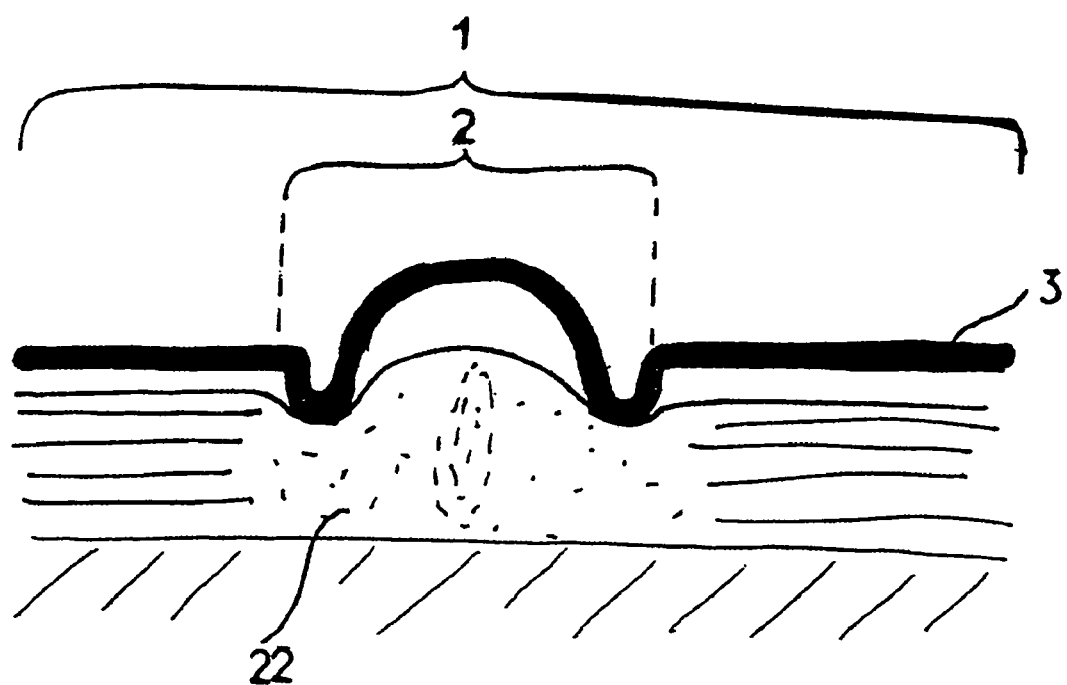

FIG. 13 shows a cross-section view of the scarring orthosis (1) centered on a therapeutic unit (2).

The scarring orthosis (1) features projections that exert differential pressures on the scar (15, 16) so as to control hypertrophy (22), anchorages (23), retractions and fibrosis. Orthosis (1) is distributed in treatment units (2) that are isolated or associated; this system can be closed or open. Reliefs are produced in a plate, preferably of elastic material (9). The reliefs constitute grooves (6) whose curve and depth regulate pressure so as to act on certain hypertrophic or keloidal scar projections as well as on deep lesions in the cicatricial derma. The transverse radius of the curvature of the groove (6), designed for contact is between 0.1 and 15 mm. Cupola (5) surpasses the plane of the plate, on one side of the groove, and it increases its elasticity in its deep plane and modulates pressures exerted there. An external force on its top reinforces this action. Elementary plate (9) is comprised of several associated layers or juxtapositions: plastics, foams, gels, silicones or any other material that confers a gradient of shore hardness and elastic powers on it that differ locally.

The current therapeutic module scrupulously administers homogeneous pressure over the entire hypertrophic surface without which the uncompressed hypertrophic areas would escape and would not develop properly. The goal is to obtain a smooth scarring on this unaesthetic curve, which is awkward and painful when pinched. A pneumatic or hydraulic system can be a contributing means for the production of an orthosis but it is neither indispensable or sufficient, because its role is that of an adjunct and it does not in any case represent the key component of the invention. It can be associated either as an activator on standard units, or connected to tubular grooves. Mechanizing the device allows it to massage the wearer. In all cases, specificity of the contact surface and its grooves must be present. Information provided in patent EP824 016 (LEUVEN K U RES § DEV; BOCK ORTHOPED IND (DE)) discourages the use of pressure due to the fact that "they impede healing" and reports a variation based on current therapeutic models, whereas the orthosis in this invention rests on the application of an innovative therapeutic model. The shape of grooves (6) transversally follows a determined curve according to the areas and depth of the scar being treated. Plate (9) is divided into several units comprising one or more grooves (6), thus creating a shape that may or may not be closed (FIG. 4). At least two grooves are in contact with the skin so as to have sufficient elastic ability to store the energy necessary to exert sufficient pressure. They are modeled in a plate (9) in the same way as the element marketed under the name ERCOFLEX®. Activator (3) allows the orthosis (1) to be fastened onto the patient and, according to the needs presented by the scar, is comprised of elements or means intended to increase the local pressure on the deep groove areas. It is comprised of a cuff C that is affixed to the edges the grooves, exerting a traction force on both sides (FIG. 3). Activator (3) and units (2) may be made of several different materials or just one. Over all or part of their support surface, these grooves may be smooth or may feature designs.

The scarring orthosis (FIG. 1) according to the invention is capable of restoring pressures so that they are targeted, oriented, and distributed, modulating its action on the areas between scars, and delineated by the abnormalities of the scar: anchorage, retraction, adhesion, hypertrophy, fibrosis by distributing the inter-scar tensions. It corrects parietal tension imbalance and contributes to the intrinsic restructuring of the scar. It features areas of high pressure (11) in the neighborhood of the low-pressure areas (12). Other than its elastic properties, it must necessarily comprise this pressure gradient. Voluntary or automatic movements during sleep, which deliver additional energy (17), activate the units and make the device more effective (FIG. 3). In case of total immobilization, there is less action but it is very useful for recently burned skin.

This orthosis (1) acts on all dermal and infra-dermal components: nerve endings, vascularization, inflammation, fibroblasts, myofibroblasts, extra cellular matrix. In a surprising manner that is not obvious, the action of orthosis (1) is rapid; for example, after 6 weeks it gives its earliest clinical results, which are not definitive but which permit some improvement to be anticipated.

Its pressure action associated with the back's original described straightness allows it to act on associated phenomena such as contractions or retractions encountered in kyphoscoliosis patients.

The scarring orthosis (1) is a device comprised of a plate (9) or plane of reference (FIG. 1); parts in positive upper relief or cupola (5), ensuring elasticity, and suppression of negative hollow or grooved reliefs (6) in contact with the scar. For a single unit (2), the orthosis is composed at least of two types of reliefs relative to the surface in contact with the skin, one negative, or grooved, side (6) encircling it, and the other positive tumescence or the cupola (5): with hollows and bumps. The groove is at least on both sides of the cupola; and preferably curled. Some grooves have a wavy surface on the bottom. The cupola (5) must be equal to or taller than the plastic reference surface (9) (FIG. 1). The form delineated by the groove (6) is advantageously in the shape of a ring and also kidney-bean shaped, or other closed shapes, which may or may not be a function of the resultant inter-scar tension that we wish to produce, and the lesion being treated. The depth of the furrows, the size and shape of the unit allow us to vary the therapeutic plane more specifically: from the dermal plane to the deeper planes. Each unit (2) creates an immobilization relative to the scar inside the surface delineated by the grooves, and has a specific action that can be doubled with a combined action if they are coupled.

The scarring orthosis comprises a plate (9) and/or an activator. It is composed of one or more materials of different shore hardnesses: devices with elastic results that are capable of storing and releasing energy. Handling units (2) are reliefs that can amplify this mechanism, while targeting and directing its action. Activators (3) and fixating cuffs precisely position the unit or units adapted for diagnosed scarring abnormalities (22, 23) and transmit or amplify an increase in pressure related to pressurizing during positioning of the orthosis or to patient movement (FIG. 3) which becomes partially therapeutic.

Activator (3) starts outside the units scar pressure delta area (FIG. 2) or sub units (4) which comprise the orthosis (FIG. 4). The scar orthosis (1) comprises at least one unit (2), but may consist of several, juxtaposed or interactive, of greatly varying sizes (FIG. 4, 9, 10). Unit (2) is an open system if it is made with dash-shaped grooves or peripheral sub-units (4). In the case of an open system (FIG. 4), unit (2) is composed of peripheral units that are equivalent to the grooves (6); the "cupola" (5) corresponds to the area located between them. This is a closed system if a single groove comprises the unit.

It is possible to make incomplete models that are less active, because they do not fulfill all the conditions described above. Units (2) can thus comprise prefabricated reliefs, which may or may not be modulatable, by crushing or injection into a recessed material; stamped wedges or cut into curls. They (2) are also riveted, screwed, fitted, and welded differently and separately to the activator. A pneumatic and hydraulic variant, which may be mechanized and intended to provide a massaging action, would be effective only if it meets the criteria of the invention and, more specifically, possess a contact surface that is active with the adapted grooves. The complete custom model is the most effective.

The interface separates the skin from the unit (2). It is reduced to a simple surface treatment of the unit component or components (2) or individualized into: silk, metalline®, cotton netting or any other material.

According to a preferred and original manner of embodiment, the orthosis may be made by fashioning it of a single material. Activator (3) and units are worked starting with a flexible plate (9) and adhesive. One of the products appropriate for making the orthosis is marketed under the name of Ercoflex® 2, 3, or 4 mm thick. First of all, a silhouette curve is made on the plate. The first cutouts take freedom of movement into consideration; if necessary, material required for fixation cuffs is reserved, which will be the starting point of the unit's edges. The cuffs are capable of positioning and transmitting energy to the grooves and cupolas. Most often, they tighten the body perpendicular to the axis of the limbs. Unit position and curves are noted, traced on the scar. The print of the unit is taken using silicone molding or any other material, and takes the curve of the body and creates the groove counter-type. A cylinder is created that is arranged on the contour of the unit drawn by the practitioner onto the patient. Once cold polymerization has taken place, this print is transferred onto the flexible thermo-formable plastic. This is mirror-image modeling, counter-type, type, negative, positive which allows the orthotic to be created. If a memory ("smart") material is being used, it is created, as often as possible, using controlled cooling in an aqueous medium, in order to conserve both elastic and mechanical properties as well as curves. At the end of this maneuver, the device is checked against the scar and a predominant support is noted on the areas corresponding to the grooves. Now the activator must be created using an adhesive tape affixed by a rivet, sewn or welded to the external edge of the groove. This creates the cuff that encloses the limb. The path of the cuffs during movements allows the action of the orthosis can be modulated.

The shapes of the orthosis, by unit or by activator, vary according to the application. So for example, the units, alone or together, treat areas of anchorage in the extremities of the adhesions. The body of the adhesion requires perpendicular stresses on the small areas. The scar plaque is encircled or, more often, split apart.

The activator carries out more than a simple cuff fastening. It can be flexible or rigid, inextensible or elastic, for example, a Velcro® (trademark) adhesive strip, or any other material that meets the needs of the area being treated. Its design is often complex and delicate (FIG. 7 to 12).

Simply stated, we have recourse to a compressive garment, custom, available retail or otherwise, of specific elasticity to allow additional overall pressure and contribute to the fastening of the orthosis.

A variation of the orthosis is in the form of an insulated flexible mask or in addition under a rigid activator mask. A flexible mask is modeled on a positive, then a rigid mask underneath. On the flexible mask, units are designed. The flexible mask worn under the rigid mask is the most effective, since it acts both on points of external pressure and on tops of cupolas. The masks may be worn together or separately, which allows cutaneous constraints to be varied. Separate units can also be permanently affixed or can be removable from the inside of the rigid mask.

The orthosis (1) associated with a hand immobilizing splint (FIG. 5) which has an activating device comprised of a rigid counter support and an elastic component; for example, a thermo-formable cap associated with materials of a low shore index like small cylinders cut out of PLASTAZOTE® which exerts pressure on the tops of the cupolas. In this orthosis, the rigid counter support forms a rigid activator mask RM and the elastic component forms a flexible mask FM. The hardness and size of the cylinders or nipples modulate the support. This device allows concavities to be treated. It can be in the form of a simple metacarpal bracelet for a burn of moderate complexity on the palm; units and activators are worked into a single plate.

Here the orthosis (1) is associated with a kyphosis corrector. The kyphosis corrector must meet the positioning requirements for the orthosis. The kyphosis corrector treats analgesic attitudes or forming kyphosis.

It is composed of an inverted T of thermoformable plastic, molded between omoplates and starting from the upper part of the T; two inextensible tufted straps surrounding the armpit hollows. The device is finished with an abdominal strap which could conceivably feature an articulated anterior valve V that molds the rib cage vents in order to enhance its corrective capacity in the case of a kyphotic attitude that is too underscored (FIG. 7, 8, 9, 10) or an analgesic or forming kyphoscoliosis.

In confirmed kyphosis, the thermo formable posterior valve will cover the sub-acromial parts of the two omoplates, without going over the top of the kyphosis (FIG. 11, 12) on top and the anterior and posterior iliac spines below. The scar orthosis thus has an optimized action on the anterior thoracic teguments.

A variation of the orthosis features concentric units but these units do not necessarily have the same center; one unit can cover one or several others; which allows treatment of large asymmetric heterogeneous scars and to achieve progress in treatment.

The orthosis can be used over all or part of the body: face, canthi, ear speculum, trunk, perineum, limbs, hands, spaces between fingers and toes, fingers, toes, feet and arches by adding units to soles.

The orthosis can be optimized during its design by tests, para-clinical examinations of scars (Doppler echo, Doppler laser to measure thickness of residual derma), to be completed by CAD or CAM computer handling which allows the shape, components and characteristics of the optimal viscoelastic system to be determined. It incorporates the calculation of the deformation induced by movements within the usual degrees of freedom of the adjacent joints.

Orthoses (1) derived from the invention can be prefabricated for a topographic contour defined using statistical data, based on the frequency of complications. They are less active than those made to order, because they are not adapted to the great individual variability associated with accidents, level of care, and individual contours. Units that are less impressive in their performance can be made of plastic, foam, gel, silicone or any other material that includes a discharge area cutout or association of materials of different shore hardnesses. A simple ring of silicone, a wavy elastic material under pressure by a compressive or banding garment that fulfills a small portion of the functions of the custom-made units. The associated activator is often rudimentary.

The action of the orthosis differs from the one that distributes pressures, such as that offered by a good anti-eschar mattress. Besides its preventive action, it has a therapeutic action that is oriented onto the scar, zone by zone.

The action of orthosis (1) is to distinguish between the action of a compressive garment (36) (FIG. 6) which distributes a staggered variable pressure on the height of the limb segments, without the possibility of modulating the pressures on the scar at a given level. The interposition of foam (37) (FIG. 6), silicone in a smooth plate traced onto the scar allows us, moreover, to increase and focus pressures in order to obtain an overall smooth scar, without variability in action or between-scar restructuring effect.

The rigid pneumatic or hydraulic mask has an action that is comparable to related garments.

A simple unit (2) under the garment is more effective, and it brings another dimension, comprised of a new selectivity of areas subjected to compression and acts beyond the scar contact surface. This can be the polymerized silicone in the fiber, or glued to compressive garments that are custom made commercially. A manufactured fabric containing, at the level of its scar surface, projections made of silicone or other material would also be only partly effective. These are nothing but incomplete derivatives of the invention.

The introduction of orthoses is done gradually by day for safety reasons. It is active starting from the third hour; beyond that, its action is proportional to the amount of time it is worn. This is very useful during introduction and during gradual weaning off the device. Progress requires that it be renewed during the $3^{rd}$ month; since the priority scale of indications has progressed. Freedom of movement can be offered to the patient several months earlier than with standard treatment. The earliest improvement seen involves flexibility. Developmental stages are in general from 3 to 6 weeks.

According to one manner of embodiment, the orthosis is made of flexible thermo formable plastic of a thickness from 1 to 4 mm. The depth of the groove and the width designed for contact are from 0.1 to 15 mm. The cupola measures between 0.2 and 25 cm in it largest diameter. In the presence of adhesions, retraction or anchorages all units are considered to be interactive.

The invention claimed is:

1. A scarring orthosis comprising a plate in which reliefs are formed; the reliefs being sized and shaped to exert differential pressure on only a portion of a scar so as to control hypertrophy, retraction and fibrosis; the reliefs being molded in an elastic plate and comprising at least one curved groove shaped to act on certain selected regions of dermal scarring thickness and at least one cupola; said groove surrounding said cupola; wherein the groove has a bottom spaced from a first side of the plane of the plate and the cupola has a top spaced from a second, opposite side of the plane of the plate such that said groove and said cupola are on opposite sides of the plane of said plate, whereby said orthosis increases the elasticity in its deep plane and modulates the force exerted there, so that it can increase pressure locally on the back of the groove when it is pushed by a treatment unit.

2. A scarring orthosis comprising a plate in which reliefs are formed; the reliefs being sized and shaped to exert differential pressure on only a portion of a scar so as to control hypertrophy, retraction and fibrosis; the reliefs being molded in an elastic plate and comprise curved grooves extending below one side of the plane of the plate and a cupola above the other side of the plane of the plate so that said grooves act on selected regions of dermal scarring thickness; said groove surrounding said cupola.

3. The orthosis of claim 1 wherein the shape of the groove follows a curve determined according to the areas and the depth of the scar to be treated.

4. A scarring orthosis comprising a plate formed of at least one differential pressure exerting relief sized and shaped to exert a varying pressure across only a portion of the scar so as to control hypertrophy; the at least one relief being molded in an elastic plate and comprising a curved dermal engaging groove defining a trough which extends below the plane of the plate and a cupola which extends above the plane of the plate so that the orthosis acts on selected regions of dermal scarring thickness; said groove surrounding said cupola; the plate being divided into several units, comprising one or more grooves that make a shape, in which at least two grooves are adapted to be arranged on the skin so as to have a coupled action that is sufficiently elastic to store and exert adequate pressure by the plate.

5. The orthosis of claim 1 including an activator comprised of a cuff that is affixed to an edge of the groove, adjoining the cupola which allows the orthosis to be affixed to the patient, and comprising a means designed to locally increase pressure in the deep areas of the grooves; said means comprising associated elastic and rigid elements to create a counter support that allows concavities to be treated.

6. The orthosis of claim 5 wherein the plate is divided into several units; the activator and units being made of the same material or different materials affixed to the edges of the units.

7. The orthosis of claim 4 wherein the orthosis comprises a single unit or a plurality of units which act together as a system; said units being made of foam or gel or any other material.

8. The orthosis of claim 4 wherein the activator and units are made of the same material or different materials affixed to edges of the units.

9. The orthosis of claim 7 wherein the grooves in combination define a shape that is closed.

10. The orthosis of claim 7 wherein the grooves in combination define a shape that is opened.

11. The orthosis of claim 4 wherein the plate is formed from a material has an elasticity and/or hardness that is locally different.

12. The orthosis of claim 11 wherein the material is a plastic, foam, gel, or silicone.

13. The orthosis of claim 4 wherein the orthosis is in the shape of an insulated flexible mask used in addition to and under a rigid mask, or a rigid mask with removable separate units.

14. The orthosis of claim 4 wherein the orthosis is associated with an original kyphoscoliosis corrector that treats analgesic attitudes.

15. The orthosis of claim 4 wherein said units each comprise a simple ring of silicone, a wavy elastic material under pressure by a compressive or banding garment.

16. The orthosis of claim 4 wherein each said unit comprises polymerized silicone in a fiber, or is glued to a compressive garment.

17. The orthosis of claim 14 wherein the original kyphoscoliosis corrector is composed of an inverted T formed of thermoformable plastic, molded between omoblades and starting from an upper part of the T, two inextensible tufted straps adapted to surround armpit hollows and an abdominal strap.

18. The orthosis of claim 17 wherein said straps include an articulated anterior valve that molds rib cage vents in order to enhance its corrective capacity in the case a kyphotic attitude that is too underscored or an analgesic or forming kyphoscoliosis.

19. The orthosis of claim 18 wherein in confirmed kyphosis, a thermoformable posterior valve is adapted to cover the sub-acromial parts of the two omoblades, without ever going over the top of the kyphosis on top and the anterior and posterior iliac spines below, the scar orthosis having an optimized action on the anterior thoracic teguments.

20. The orthosis of claim 7 wherein said units are comprised of an association of materials of different shore hardness values.

21. The orthosis of claim 7 wherein said units slide or are glued under a compressive garment.

* * * * *

UNITED STATES PATENT AND TRADEMARK OFFICE
CERTIFICATE OF CORRECTION

PATENT NO. : 7,540,850 B2  
APPLICATION NO. : 10/488832  
DATED : June 2, 2009  
INVENTOR(S) : Michael Guillot It is certified that error appears in the above-identified patent and that said Letters Patent is hereby corrected as shown below:

Column 2, line 59, the word "bum", should be --burn--

Signed and Sealed this

Twenty-fifth Day of August, 2009

David J. Kappos  
*Director of the United States Patent and Trademark Office*